US011234675B2

(12) United States Patent
Bocca et al.

(10) Patent No.: US 11,234,675 B2
(45) Date of Patent: Feb. 1, 2022

(54) SONAR-BASED CONTACTLESS VITAL AND ENVIRONMENTAL MONITORING SYSTEM AND METHOD

(71) Applicant: Robert Bosch GmbH, Stuttgart (DE)

(72) Inventors: Maurizio Bocca, Sunnyvale, CA (US); Fabian Henrici, Sunnyvale, CA (US)

(73) Assignee: Robert Bosch GmbH, Stuttgart (DE)

( * ) Notice: Subject to any disclaimer, the term of this patent is extended or adjusted under 35 U.S.C. 154(b) by 598 days.

(21) Appl. No.: 16/086,782

(22) PCT Filed: Mar. 28, 2017

(86) PCT No.: PCT/EP2017/057280
§ 371 (c)(1),
(2) Date: Sep. 20, 2018

(87) PCT Pub. No.: WO2017/167731
PCT Pub. Date: Oct. 5, 2017

(65) Prior Publication Data
US 2019/0099156 A1    Apr. 4, 2019

Related U.S. Application Data

(60) Provisional application No. 62/314,121, filed on Mar. 28, 2016.

(51) Int. Cl.
*A61B 8/00* (2006.01)
*A61B 5/00* (2006.01)
(Continued)

(52) U.S. Cl.
CPC ............ *A61B 8/42* (2013.01); *A61B 5/02438* (2013.01); *A61B 5/0816* (2013.01);
(Continued)

(58) Field of Classification Search
CPC ........ A61B 2560/0242; A61B 5/02438; A61B 5/0816; A61B 5/11; A61B 5/1113;
(Continued)

(56) References Cited

U.S. PATENT DOCUMENTS

2013/0030257 A1    1/2013    Nakata et al.

FOREIGN PATENT DOCUMENTS

DE    10 2014 218 140 B3    3/2016
WO        2010/036700 A1    4/2010

OTHER PUBLICATIONS

International Search Report corresponding to PCT Application No. PCT/EP2017/057280, dated Jul. 11, 2017 (3 pages).
(Continued)

*Primary Examiner* — Mark D Remaly
(74) *Attorney, Agent, or Firm* — Maginot, Moore & Beck LLP

(57) ABSTRACT

A sonar-based contactless monitoring system comprises a sonar system (308), a contactless sensing assembly (310), and a controller (302) configured to read out measurements transmitted by the sonar system and the contactless sensing assembly and calculate posture and activity of a subject. The sonar system may include a microphone (314) and a speaker (316), wherein the microphone is configured to sense a first acoustic signal in a frequency range associated with the sound and/or motion made by the subject, and a second acoustic signal in a frequency range associated with the reflection of an acoustic signal transmitted by the speaker. The contactless sensing assembly senses at least one of vital and environmental conditions, such as a heart rate, respiratory rate, activity, snoring, subject's position, and subject's movement, or noise level, weather condition, light exposure, time and radiation level.

18 Claims, 4 Drawing Sheets

(51) Int. Cl.
*A61B 5/024* (2006.01)
*A61B 5/08* (2006.01)
*A61B 5/11* (2006.01)
*A61B 7/00* (2006.01)

(52) U.S. Cl.
CPC .......... *A61B 5/1113* (2013.01); *A61B 5/1116* (2013.01); *A61B 5/1118* (2013.01); *A61B 5/4806* (2013.01); *A61B 5/6897* (2013.01); *A61B 5/6898* (2013.01); *A61B 8/00* (2013.01); *A61B 5/11* (2013.01); *A61B 5/6802* (2013.01); *A61B 5/6887* (2013.01); *A61B 7/00* (2013.01); *A61B 2560/0242* (2013.01)

(58) Field of Classification Search
CPC ... A61B 5/1116; A61B 5/1118; A61B 5/4806; A61B 5/6802; A61B 5/6887; A61B 5/6897; A61B 5/6898; A61B 7/00; A61B 8/00; A61B 8/42
See application file for complete search history.

(56) References Cited

OTHER PUBLICATIONS

Nandakumar et al.; Contactless Sleep Apnea Detection on Smartphones; MobiSys '15, May 18-22, 2015, Florence, Italy (13 pages).
Heldt et al.; Evaluation of Ultrasound-Based Sensor to Monitor Respiratory and Nonrespiratory Movement and Timing in Infants; IEEE Transactions on Biomedical Engineering; Mar. 2016; pp. 619-629; vol. 63, Issue No. 3; IEEE (11 pages).
Genc et al.; Continuous Remote Vital Sign/Environment Monitoring for Returning Soldier Adjustment Assessment; 33rd Annual International Conference of the IEEE EMBS; Aug. 30-Sep. 3, 2011; pp. 2216-2219; IEEE (4 pages).

SONAR-BASED CONTACTLESS VITAL AND ENVIRONMENTAL MONITORING SYSTEM AND METHOD

CROSS-REFERENCE TO RELATED APPLICATIONS

This application is a 35 U.S.C. § 371 National Stage Application of PCT/EP2017/057280, filed on Mar. 28, 2017, which claims the benefit of U.S. Provisional Application No. 62/314,121 filed Mar. 28, 2016, the disclosures of which are herein incorporated reference in their entirety.

FIELD

This disclosure relates to generally to a sonar-based contactless vital and environmental system and method.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Embodiments of the disclosure related to a sonar-based contactless monitoring system for monitoring vital and environmental conditions. The contactless monitoring system includes a sonar system and a contactless sensing assembly communicatively coupled to a controller having a state engine that is configured to read out a plurality of measurements transmitted by the sonar system and the contactless sensor assembly, calculate vitals such as HR and RR, posture and/or activity of a subject associated with the plurality of the measurements, and switch monitoring interface between non-contact sensors within the contactless sensor assembly and contact sensors. Additionally, the controller is configured to send and receive the plurality of measurements including at least one or more of the subject's heart rate, respiratory rate, activity, snoring, and so forth to any devices over a network.

In one embodiment, the sonar system includes a microphone and a speaker. The speaker transmits acoustic waves defines as a first acoustic signal in a frequency to a subject and the microphone senses a second acoustic signal in a frequency range that associated with at least one of the sound and motion made by the subject while the subject is either resting, napping, or sleeping in real time. In one example, the acoustic waves emitted by the speaker is at 18 kHz, although any frequency range either ultrasonic or infrasonic frequency is possible depending on the application. The first and second acoustic signals defined as first and second measurement data. A controller of the contactless monitoring system reads out the first and second measurement data collected by one of the sonar system, calculates posture and activity of a subject associated with the first and second measurement data, and switches the monitoring interface between non-contact sensors within the contactless sensor assembly and contact sensors. In some embodiments, the contactless sensing assembly senses vital and environmental conditions, converts the sensed conditions to an electrical signal defined as measurement data, and then transmits the converted electrical signal to the controller for processing. The controller of the contactless monitoring system reads out the measurement data collected by the contactless sensing assembly, calculates posture and activity of a subject associated with the first and second measurement data, and switches the monitoring interface between the non-contact sensors within the contactless sensor assembly and contact sensors.

In yet another embodiment, the contactless sensing assembly senses vital and environmental conditions, converts the sensed conditions to an electrical signal defined as a third measurement data, and then transmits the converted electrical signal to the controller for processing. The controller of the contactless monitoring system reads out first, second, and third measurement data collected by the sonar system and the contactless sensing assembly, calculates posture and activity of a subject associated with the first and second measurement data, and switches the monitoring interface between the non-contact sensors within the contactless sensor assembly and contact sensors. The measurement data may be vital conditions including one or more of the subject's heart rate, respiratory rate, activity, snoring, subject's voice stress level, subject's position, subject's movement, and any subject's physiological status. In alternate embodiment, the contactless monitoring system monitors health and physiological conditions and environmental conditions throughout a period, such as the day, week, month, and year. The detected health and physiological conditions and environmental conditions may be stored in a transitory or non-transitory machine readable medium of the contactless monitoring system for analyzing and processing by the controller before the data is transmitted and shared with another device, a server, and combination over a network. Additionally, the data stored in the transitory or non-transitory machine readable medium for analyzing and processing by the controller may be transmitted for display on the input/output interface. Since voice, breath, heart, and environmental sounds are typically in differently frequency bands, signal separation techniques could be used to allow separation of various forms of sound. The signal separation techniques may include software, algorithm, digital signal processing unit, noise cancellation processing unit, sound analyzer, and the like. The controller is configured to send the plurality of measurements including at least one or more of the subject's heart rate, respiratory rate, activity, snoring, and the like for display on a display screen in a human readable format. The format can be in the form of text, image, icon, graph, chart, and the like, either in color or black and white. An audible or sound in addition to human readable format displayed on the display may be transmitted to a transducer of the contactless monitoring system 408. The transducer may be the speaker or a different speaker encapsulated in the same contactless monitoring system.

In further embodiment, the contactless monitoring system includes a security mode to detect intrusion or unauthorized subject into a site using the sonar system.

BRIEF DESCRIPTION OF THE DRAWINGS

These and other features, aspects, and advantages of this disclosure will become better understood when the following detailed description of certain exemplary embodiments is read with reference to the accompanying drawings in which like characters represent like arts throughout the drawings, wherein.

DETAILED DESCRIPTION

The following description is presented to enable any person skilled in the art to make and use the described embodiments, and is provided in the context of a particular application and its requirements. Various modifications to the described embodiments will be readily apparent to those skilled in the art, and the general principles defined herein may be applied to other embodiments and applications without departing from the spirit and scope of the described embodiments. Thus, the described embodiments are not limited to the embodiments shown, but are to be accorded the widest scope consistent with the principles and features disclosed herein.

Figure 1:
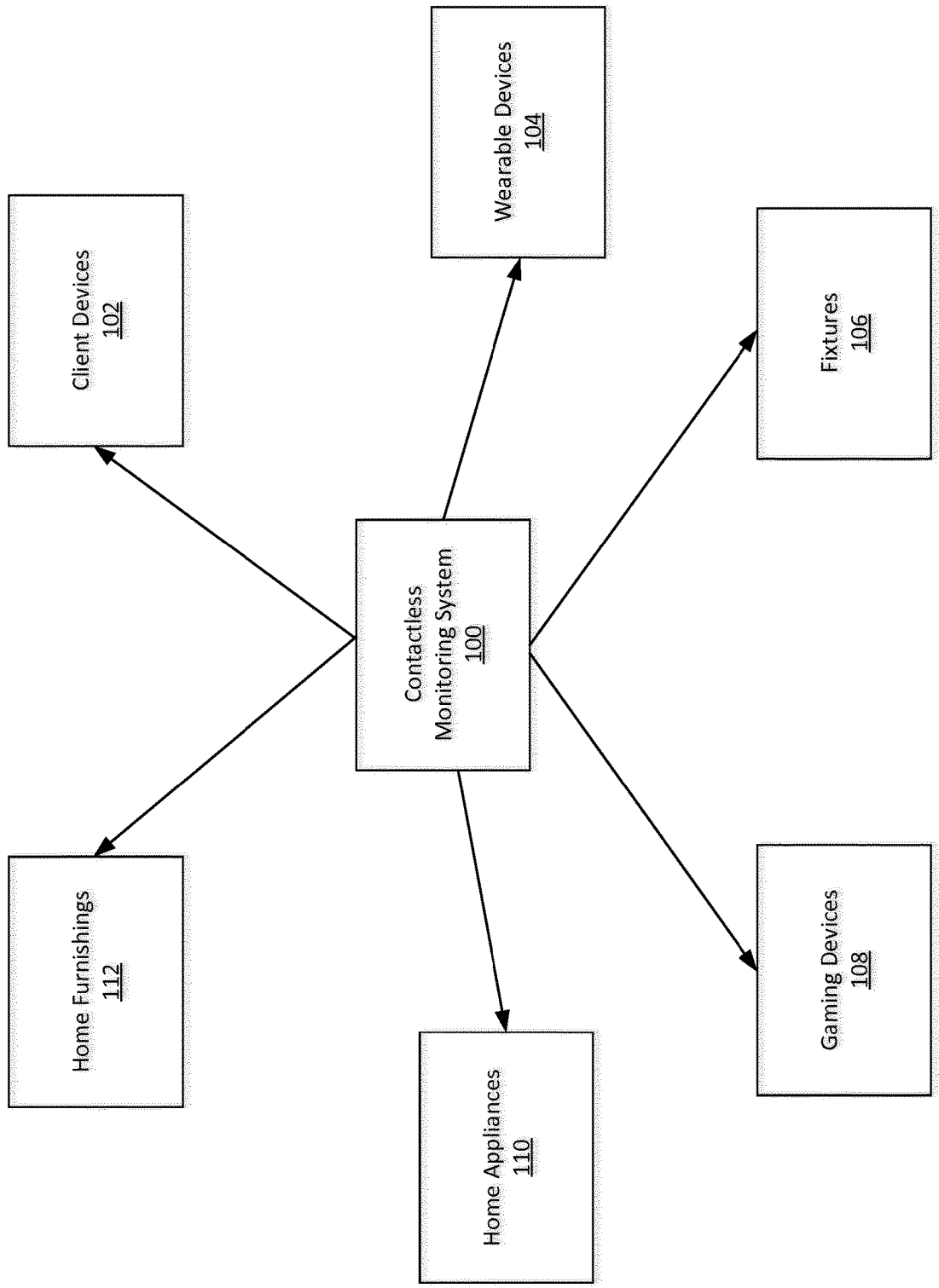
FIG. 1 illustrates a block diagram of a contactless monitoring system which may be used as a single device or integrated into another devices according to several embodiments of the disclosure.

FIG. 1 illustrates a contactless monitoring system 100 according to several embodiments of the disclosure. The monitoring system 100 includes at least one of a sonar system and contactless sensor assembly (illustrated in FIG. 3) configured to monitor and measure one or more of vital and environmental conditions of a subject in real-time while the subject is either resting, napping, or sleeping. Vital conditions or signs may include, respiration, heart rate, breath rate, subject's voice stress levels, subject's position, subject's movement, subject's physiological status, and so forth. Environmental conditions may include noise level, weather condition (such as and so forth. The contactless monitoring system 100 may come in different size and shape, depending on the applications. In one embodiment, the contactless monitoring system 100 is a stand-alone device. In some embodiments, the contactless monitoring system 100 is integrated into another devices such as a client devices 102, wearable devices 104, fixtures 106, gaming devices 108, home appliances 110, home furnishings 112, and so forth. In another embodiment, the contactless monitoring system 100 may be integrated into more than one devices. The client device 102 may be a cellular phone, a tablet, a personal computer, a personal digital assistant, a laptop, a scanner, a printer, a thermostat, a smoke detector, a media player, and the like. The wearable device 104 may be a watch, jewelry (such as a ring, a bracelet, a neckless), a belt, a hairband, a hair clip, an earpiece, a headset, a listening device, a wristband, and the like. The fixture 106 may be a lighting fixture, a fan fixture, an on/off switch, an alarm clock, a wall clock, and the like. The gaming device 108 may be a game controller, a game station, a handheld game, a joystick, and the like. The home appliance 110 may be a television, a loud speaker, a speaker box, a remote control, and the like. The home furnishing 112 may be a bed headframe or headboard, a nightstand, a couch, a table, a chair, a mattress, a pillow, and the like.

Figure 2:
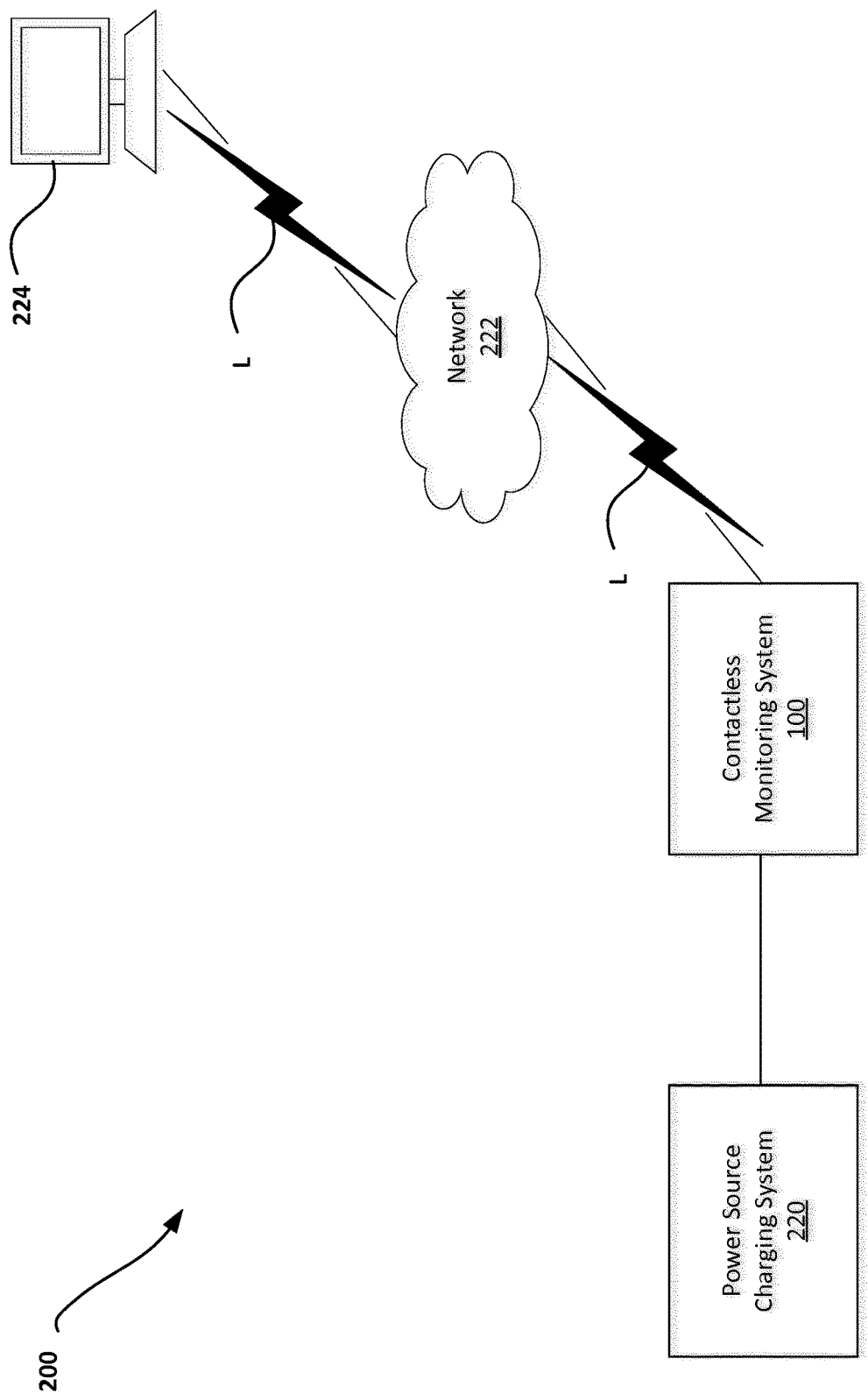
FIG. 2 illustrates a simplified block diagram of the contactless monitoring system of FIG. 1 used in a network architecture environment.

Now referring to FIG. 2, the contactless monitoring system 100 of FIG. 1 is operated in a network architecture environment 200. A network 222 is communicatively coupled the contactless monitoring system 100 to a server 224 via a communication link L. The communication link L with the server 224 and the contactless monitoring system 100 may be achieved through wired, wireless (such as fixed wireless, mobile wireless, portable wireless, and IR wireless), or combination thereof. The wireless communication link may include cellular protocol, data packet protocol, radio frequency protocol, satellite band, infrared channel, or any other protocol able to transmit data among the server 224 and the contactless monitoring system 100. For example, the wireless communication link may be Bluetooth 4.0 protocol, Bluetooth Low Energy (BLE) protocol, radio frequency identification (RFID) protocol, near field communication (NFC) protocol, far field communication (FFC) protocol, ZigBee protocol, Infrared (IR) protocol, ultra wide band (UWB) protocol, FeliCa protocol, WLAN protocol, WIFI protocol, ZWAVE protocol, WiMAX protocol, satellite protocol, AMPS protocol, TDMA protocol, CDMA protocol, GSM protocol, GPRS protocol, UMTS protocol, LTE protocol or any other cellular protocol. The wired communication link may include any wired connection link such as USB. Although only one contactless monitoring system 100 communicatively coupled to one of the network 222 and the server 224, more than one contactless monitoring system may be communicatively coupled the network, the server 224, and the contactless monitoring system 100. For example, the second contactless monitoring system is either another stand-alone device or integrated into one of a client devices 102, wearable devices 104, fixtures 106, gaming devices 108, home appliances 110, home furnishings 112, and so forth, as described above in FIG. 1.

The contactless monitoring system 100 and other devices 102, 104, 106, 108, 110, 112 with or without integrated contact monitoring system may interact with one another either via the network 222 or the server 224 where tasks are performed by the other devices and shared the data among the devices. The interaction between the devices 100, 102, 104, 106, 108, 110, 112 may be achieved over one server 224 or one network 222. In some embodiments, more than one server 224 and/or one network 222 may be communicatively coupled to the devices 100, 102, 104, 106, 108, 110, 112. The devices can in some embodiments be referred to as a single client machine or a single group of client machines, while the server 224 may be referred to as a single server or a single group of servers. In some embodiments, the contactless monitoring system 100 is a cloud computing device which may be communicated with via the Internet, and which may be co-located or geographically distributed, wherein shared resources, software, and information are provided to computers and other devices on demand for example, as will be appreciated by those skilled in the art.

The server 224 may be an application server, a certificate server, a mobile information server, an e-commerce server, a FTP server, a directory server, CMS server, a printer server, a management server, a mail server, a public/private access server, a real-time communication server, a database server, a proxy server, a streaming media server, or the like. The network 222 can comprise one or more sub-networks, and can be installed between the contactless monitoring system 100 and the server 224 within the network architecture environment 200. In some embodiments, the network 222 can be for example a local-area network (LAN), a metropolitan area network (MAN), a wide area network (WAN), a primary network comprised of multiple sub-networks located between the contactless monitoring system 100 and the server 224, a primary public network with a private sub-network, a primary private network with a public sub-network, or a primary private network with a private sub-network 222. Still further embodiments include a network 222 that can be any network types such as a point to point network, a broadcast network, a telecommunication network, a data communication network, a computer network, an ATM (Asynchronous Transfer Mode) network, a SONET (Synchronous Optical Network) network, a SDH (Synchronous Digital Hierarchy) network, a wireless network, a wireline network, a cloud network, and the like. Depending on the application, other networks may be used so that data exchanged between the client machine and the server can be transmitted over the network. Network topology of the network 222 can differ within different embodiments which may include a. bus network topology, a star network topology, a ring network topology, a repeater-based network topology, or a tiered-star network topology. Additional embodiments may include a network of mobile telephone networks that use a protocol to communicate among client devices, where the protocol can be for example AMPS, TDMA, CDMA, GSM, GPRS, UMTS, LTE or any other protocol able to transmit data among client devices.

The contactless monitoring system 100 may be battery operated and an optional wired connection is provided to charge the battery. As illustrated, a power source docking system or a power source charging system 220 may receive power, charge, and power the contactless monitoring system 100 is provided. The power source charging system 220 may be, for example, an inductive charger, a solar charger, an optical charger, a microwave charger, an electromagnetic charger, an electrical charger, or any type of chargers for receiving power from external source and then charging and powering the contactless monitoring system 100. The power source charging system 220 may provide a unified interface with various standards of wireless charging such as Qi or other standards. The charging system 220 converts the various received power signals (such as an optical signal) into a standard format (such as an electrical signal) for charging the contactless monitoring system 100, and vice versa. The charging system 220 may also convert the received power signal to a higher voltage potential or a lower voltage potential. The charging system 220 may be a standalone device, in one embodiment. In some embodiments, the charging system 220 may be integrated into another device such as a home furnishing (e.g. a table). Although one charging system 220 for receiving power, and charging and powering the contactless monitoring system 100 is illustrated, more than one charging system 220 may be provided to charge and power a plurality of contactless monitoring systems simultaneously.

Figure 3:
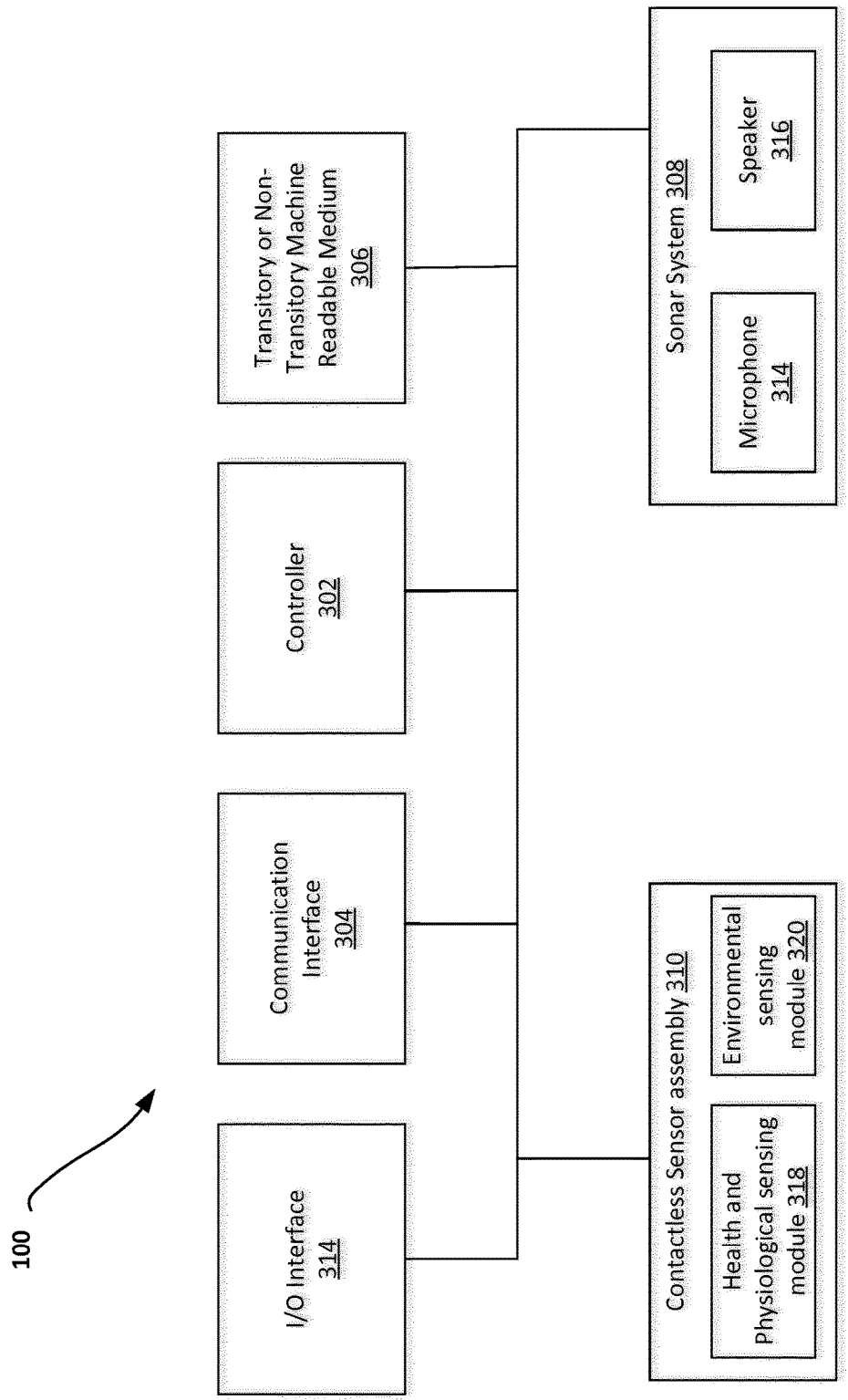
FIG. 3 illustrates a simplified schematic diagram of the contactless monitoring system of FIG. 1.

FIG. 3 illustrates a simplified schematic diagram of the contactless monitoring system 100 of FIG. 1. The system 100 includes a system interface bus 322 for communicatively coupling various computer implemented modules. The modules include a controller 302, a communication interface 304, a transitory or non-transitory machine readable medium 306, a sonar system 308, a contactless sensor assembly 310, and an input/output interface 312. Depending on the applications, any type of computer implemented modules may be integrated into the contactless monitoring system 100. The system interface bus 322 may be any types of bus structures including a peripheral bus, a local bus, and any type of bus architectures. The controller 302 may be a general or special purpose microprocessor or processor operating under control of computer executable instructions, such as program modules or software for operating the computer implemented devices operably connected thereto, such as the transitory or non-transitory machine readable medium 306, the communication interface 304, the acoustic assembly 308, the contactless sensor assembly 310, and the input/output interface 312. The controller 302 also enables execution of software programs using various operating systems including, but not limited to, the iOS and Android operating systems. Example of various types of processor include computer processing units (CPU), graphics processing units (GPU), accelerated processing units (APU), digital signal processors (DSP), and the like. Program modules generally include routines, programs, objects, components, data structure and the like that perform particular tasks or implement particular abstract types. In one embodiment, some or all of the sub-processors may be implemented as computer software tangibly stored in a memory to perform their respective functions when executed. In alternate embodiment, some or all of the sub-processors may be implemented in an ASIC. As illustrated, the controller 302 include a processor having a state engine that is configured to read out a plurality of measurements transmitted by the sonar system 308 and the contactless sensor assembly 310, calculate posture and activity of a subject associated with the plurality of the measurements, and switch monitoring interface between non-contact sensors within the contactless sensor assembly 310 and contact sensors. Additionally, the controller 302 is configured to send and receive the plurality of measurements including at least one or more of the subject's heart rate, respiratory rate, activity, snoring, and so forth to one or more of the contactless monitoring systems, client devices, wearable devices, fixtures, gaming devices, home appliances, home furnishings, and so forth over a network and/or a server via the communication interface 304.

The communication interface 304 typically includes computer readable instructions, data structures, program modules, or other data in a modulated data signal such a carrier wave or other transport mechanism and include any information delivery media. The form of signals may be, for example, electronic, electromagnetic, optical, or other signals capable of being received by the communication interface 304. The communication interface 304 may also include wired media such as a wired network or direct-wired communication, fixed wireless media, and wireless media such as acoustic, RF, infrared (IR) and the like, cellular wireless media, portable wireless, or combination thereof. Communications of the any of the above should also be included with the scope of the transitory or non-transitory machine readable medium 306. The transitory or non-transitory machine readable medium 306 may be partitioned or otherwise mapped to reflect the boundaries of the various subcomponents. The transitory or non-transitory machine readable medium 306 typically includes both volatile and non-volatile media, removable and non-removable media. For example, the transitory or non-transitory machine readable medium 306 includes computer storage media and communication media. Computer storage media includes both volatile and nonvolatile, removable and non-removable media implemented in any method or technology, CD-ROM, DVD, optical disk storage, magnetic cassettes, magnetic tape, magnetic disk storage or other magnetic storage device, or any other medium which can be used to store the desired information and which can accessed by a client machine. For example, computer storage media can include a combination of random access memory (RAM), read only memory (ROM) such as BIOS.

The sonar system 308 includes a microphone 314 and a speaker 316. Other suitable sonic devices such as a piezoelectric transceiver may be used. The microphone 314 is configured to sense a first acoustic signal in a frequency range that associated with at least one of the sound and motion made by the subject using the contactless monitoring system 100 and a second acoustic signal in a frequency range that associated with the reflection of the second acoustic signal transmitted by the speaker 316. The first and second acoustic signals defined as first and second measurement data. The controller 302 reads out the first and second measurement data, calculates posture and activity of a subject associated with the first and second measurement data, and switches the monitoring interface between the non-contact sensors within the contactless sensor assembly 310 and the contact sensors. Depending on the application, more than one microphone and speaker may be integrated into the contactless monitoring system as a second sonar system. In some embodiments, additional microphone functions as a noise cancelling microphone may be integrated in the contactless monitoring system.

The contactless sensor assembly 310 configured to monitor health and physiological conditions and environmental conditions in real-time includes a health physiological sensing module 318 and an environmental sensing module 320. The health physiological sensing module 318 is configured to detect and measure health and physiological conditions or vital signs of the subject in a vicinity of the subject while resting or sleeping and closes to the contactless monitoring system 100. The health and physiological conditions include heart rate, pulse rate, breathing rate, heartbeat signatures, and so forth. The environmental sensing module 320 is also configured to detect and measure environmental condition in the vicinity of the subject while resting or sleeping and closes to the contactless monitoring system 100. The contactless sensor assembly 310 further includes a body sensing module configured to detect and measure subject's position and subject's movement while resting or sleeping. The detected health and physiological conditions and environmental conditions throughout a period, such as the day, week, month, and year may be stored in the transitory or non-transitory machine readable medium 306 for analyzing and processing by the controller 202 before the data is transmitted and shared with another device, a server, and combination over a network. The data stored in the transitory or non-transitory machine readable medium 306 for analyzing and processing by the controller 202 may be transmitted for display on the input/output interface 312. The contactless sensor may include ECG sensor, EEG sensor, respiratory sensor, accelerometer sensor, navigation sensor, body sensor, motion sensor, temperature sensor, optical sensor, and any physiological and environmental sensors. Since voice, breath, heart, and environmental sounds are typically in differently frequency bands, signal separation techniques could be used to allow separation of various forms of sound. The signal separation techniques may include software, algorithm, digital signal processing unit, noise cancellation processing unit, sound analyzer, and the like.

The input/output interface 312 includes various end user interfaces such as a display, a keyboard, joystick, a mouse, a trackball, a touch pad, a touch screen or tablet input, a foot control, a servo control, a game pad input, an infrared or laser pointer, a camera-based gestured input, and the like capable of controlling different aspects of the machine operation. For example, user can input information by typing, touching a screen, saying a sentence, recording a video, or other similar inputs. As described earlier, the controller 302 is configured to send the plurality of measurements including at least one or more of the subject's heart rate, respiratory rate, activity, snoring, and the like for display on a display screen 312 in a human readable format. The format can be in the form of text, image, icon, graph, chart, and the like, either in color or black and white. An audible or sound in addition to human readable format displayed on the display 312 may be transmitted to a transducer of the contactless monitoring system 100. The transducer may be the speaker 316 or a different speaker encapsulated in the same contactless monitoring system 100.

Figure 4:
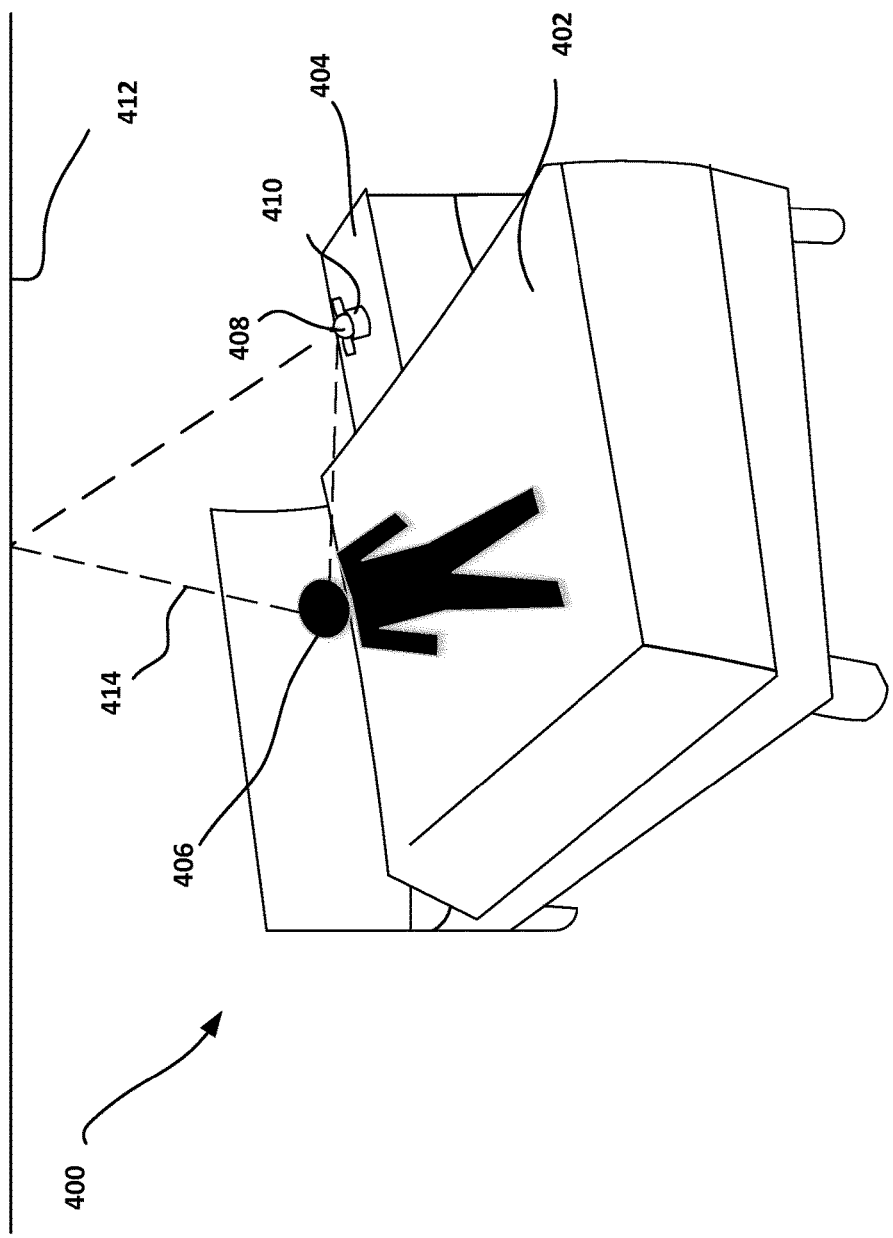
FIG. 4 illustrates an embodiment of the contactless monitoring system.

FIG. 4 illustrates one embodiment of a contactless monitoring system 408 mounted on a charging station 410 in a bed room 400. As can be seen, a subject 406 laid on a bed 402 sleeping. Adjacent to the bed is a nightstand 404 and the contactless monitoring system 408 mounted on a charging station 410 are found on the nightstand 404. The contactless monitoring system 408 is identical to the contactless monitoring system 100 of FIG. 3 and includes a sonar system having a microphone and a speaker and a contactless sensing assembly. The speaker transmits acoustic waves 414 defines as a first acoustic signal in a frequency to the subject 406 and the microphone senses a second acoustic signal in a frequency range that associated with at least one of the sound and motion made by the subject 406 while the subject is either resting, napping, or sleeping in real time. In one example, the acoustic waves emitted by the speaker is at 18 kHz, although any frequency range either ultrasonic or infrasonic frequency is possible depending on the application. The first and second acoustic signals defined as first and second measurement data. A controller of the contactless monitoring system 408 reads out the first and second measurement data collected by one of the sonar system, calculates posture and activity of a subject associated with the first and second measurement data, and switches the monitoring interface between non-contact sensors within the contactless sensor assembly and contact sensors. In some embodiments, the contactless sensing assembly senses vital and environmental conditions, converts the sensed conditions to an electrical signal defined as measurement data, and then transmits the converted electrical signal to the controller for processing. The controller of the contactless monitoring system 408 reads out the measurement data collected by the contactless sensing assembly, calculates posture and activity of a subject associated with the first and second measurement data, and switches the monitoring interface between the non-contact sensors within the contactless sensor assembly and contact sensors.

In another embodiments, the contactless sensing assembly senses vital and environmental conditions, converts the sensed conditions to an electrical signal defined as a third measurement data, and then transmits the converted electrical signal to the controller for processing. The controller of the contactless monitoring system 408 reads out first, second, and third measurement data collected by the sonar system and the contactless sensing assembly, calculates posture and activity of a subject associated with the first and second measurement data, and switches the monitoring interface between the non-contact sensors within the contactless sensor assembly and contact sensors. The measurement data may be vital conditions including one or more of the subject's heart rate, respiratory rate, activity, snoring, ECG level, EEG level, blood oxygenation, subject's voice stress level, subject's body temperature, subject's position, subject's movement, and any subject's physiological status. In addition, the measurement data may be environmental conditions including noise level, weather condition (such as temperature, humidity, air quality, and pollen count), light exposure, time (day or night), radiation level, and so forth.

The contactless monitoring system 408 may monitor health and physiological conditions and environmental conditions throughout a period, such as the day, week, month, and year. The detected health and physiological conditions and environmental conditions may be stored in a transitory or non-transitory machine readable medium of the contactless monitoring system for analyzing and processing by the controller before the data is transmitted and shared with another device, a server, and combination over a network. Additionally, the data stored in the transitory or non-transitory machine readable medium for analyzing and processing by the controller 202 may be transmitted for display on the input/output interface 312. Since voice, breath, heart, and environmental sounds are typically in differently frequency bands, signal separation techniques could be used to allow separation of various forms of sound. The signal separation techniques may include software, algorithm, digital signal processing unit, noise cancellation processing unit, sound analyzer, and the like. The controller is configured to send the plurality of measurements including at least one or more of the subject's heart rate, respiratory rate, activity, snoring, and the like for display on a display screen in a human readable format. The format can be in the form of text, image, icon, graph, chart, and the like, either in color or black and white. An audible or sound in addition to human readable format displayed on the display may be transmitted to a transducer of the contactless monitoring system 408. The transducer may be the speaker or a different speaker encapsulated in the same contactless monitoring system 408.

The contactless monitoring system 408 further includes a security mode, where a room is monitored via sonar technology. This can be used for intrusion detection by using speaker as siren and/or send wireless alarm. The difference in heart or respiratory rate between humans and animals also allows for error-free differentiation between the two, e.g. alarm sounds only if pet enters the room, but not if human does.

The embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling with the sprit and scope of this disclosure.

While the patent has been described with reference to various embodiments, it will be understood that these embodiments are illustrative and that the scope of the disclosure is not limited to them. Many variations, modifications, additions, and improvements are possible. More generally, embodiments in accordance with the patent have been described in the context or particular embodiments. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A sonar-based contactless monitoring system for monitoring a subject, comprising:
    a sonar system for sensing a first measurement of a plurality of measurements;
    a contactless sensing assembly for sensing a second measurement of the plurality of measurements; and
    a controller communicatively coupled to one of the sonar system and the contactless sensing assembly, the controller configured (i) to read out the plurality of measurements, and (ii) to calculate posture and activity of the subject based on the plurality of the measurements.

2. The sonar-based contactless monitoring system of claim 1 wherein the plurality of measurements includes at least one of vital conditions and environmental conditions.

3. The sonar-based contactless monitoring system of claim 2 wherein the vital conditions include one or more of a heart rate, respiratory rate, activity, snoring, ECG level, EEG level, blood oxygenation, subject's voice stress level, subject's body temperature, subject's position, and subject's movement.

4. The sonar-based contactless monitoring system of claim 2 wherein the environmental conditions include one or more of noise level, weather condition, light exposure, time, and radiation level.

5. The sonar-based contactless monitoring system of claim 1 wherein the sonar system comprises:
    a speaker configured to transmit a first acoustic signal to the subject; and
    a microphone configured to sense a second acoustic signal in a frequency range associated with at least one of sound and motion made by the subject while the subject is either resting, napping, or sleeping in real time,
    wherein the first measurement is based on the second acoustic signal.

6. The sonar-based contactless monitoring system of claim 5 wherein the first acoustic signal is either an ultrasonic frequency or an infrasonic frequency.

7. The sonar-based contactless monitoring system of claim 1 further comprising:
    a transitory or non-transitory machine readable medium configured to store the first measurement and the second measurement.

8. The sonar-based contactless monitoring system of claim 1 further comprising:
    a display screen operably connected to the controller,
    wherein the controller is configured to transmit the plurality of measurements to the display screen for display in a human readable format.

9. The sonar-based contactless monitoring system of claim 8 wherein the human readable format is selected from a group consisting of text, image, icon, graph, and chart.

10. The sonar-based contactless monitoring system of claim 1 wherein the controller is further configured to implement a security mode configured to detect intrusion into a site at which the subject is located.

11. A method for sonar-based contactless monitoring of a subject, comprising:
    sensing, by a sonar system, a first measurement;
    sensing, by a contactless sensing assembly, a second measurement, at least one of the sonar system and the contactless sensing assembly coupled to a controller;
    reading out the first measurement and the second measurement with the controller; and
    determining posture and activity of the subject associated with the first measurement and the second measurement with the controller.

12. The method of claim 11 wherein the first measurement and the second measurement include at least one of vital conditions and environmental conditions.

13. The method of claim 12 wherein the vital conditions include one or more of a heart rate, respiratory rate, activity, snoring, ECG level, EEG level, blood oxygenation, subject's voice stress level, subject's body temperature, subject's position, and subject's movement.

14. The method of claim 12 wherein the environmental conditions include one or more of noise level, weather condition, light exposure, time, and radiation level.

15. The method of claim 11 further comprising:
    transmitting, by a speaker of the sonar system, a first acoustic signal to the subject; and sensing, by a microphone of the sonar system, a second acoustic signal in a frequency range that associated with at least one of sound and motion made by the subject while the subject is either resting, napping, or sleeping in real time, wherein the first measurement is based on the second acoustic signal.

16. The method of claim 15 wherein the first acoustic signal is either an ultrasonic frequency or an infrasonic frequency.

17. The method of claim 11 further comprising:

storing, by a transitory or non-transitory machine readable medium, the first measurement and the second measurement.

18. The method of claim 11 further comprising:

detecting intrusion into a site at which the subject is located with the controller operating in a security mode.

* * * * *